(12) United States Patent
Lee et al.

(10) Patent No.: US 11,364,073 B2
(45) Date of Patent: Jun. 21, 2022

(54) CARDIAC MAP SEGMENTATION

(71) Applicant: BIOSENSE WEBSTER (ISRAEL) LTD., Yokneam (IL)

(72) Inventors: Christopher Lee, Newport Beach, CA (US); Morris Ziv-Ari, Atlit (IL); Noam Seker Gafni, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 165 days.

(21) Appl. No.: 16/280,195

(22) Filed: Feb. 20, 2019

(65) Prior Publication Data
US 2020/0261150 A1    Aug. 20, 2020

(51) Int. Cl.
| | |
|---|---|
| A61B 18/14 | (2006.01) |
| A61B 5/00 | (2006.01) |
| A61B 5/287 | (2021.01) |
| G16H 50/50 | (2018.01) |
| A61B 18/00 | (2006.01) |

(52) U.S. Cl.
CPC .......... *A61B 18/1492* (2013.01); *A61B 5/287* (2021.01); *A61B 5/6853* (2013.01); *A61B 5/7435* (2013.01); *A61B 2018/00351* (2013.01); *A61B 2018/00577* (2013.01); *A61B 2018/00839* (2013.01); *G16H 50/50* (2018.01)

(58) Field of Classification Search
CPC .......................... A61B 18/1492; A61B 5/0422
See application file for complete search history.

(56) References Cited

U.S. PATENT DOCUMENTS

| | | | |
|---|---|---|---|
| 6,317,631 B1 | 11/2001 | Ben-Haim et al. | |
| 2008/0262814 A1* | 10/2008 | Zheng | G16Z 99/00 703/11 |
| 2012/0004547 A1* | 1/2012 | Harks | A61B 8/486 600/439 |

(Continued)

FOREIGN PATENT DOCUMENTS

WO    WO2012067682 A1    5/2012

OTHER PUBLICATIONS

European Search Report for corresponding EPA No. 20158218.6 dated May 25, 2020.

*Primary Examiner* — Rex R Holmes
*Assistant Examiner* — Jennifer L Ghand
(74) *Attorney, Agent, or Firm* — Dergosits & Noah LLP; Todd A. Noah

(57) ABSTRACT

One embodiment includes a cardiac ablation system, including an ablation probe including at least one ablation application element to ablate tissue in a chamber of a heart of a living subject, a tracking module to track a position of the at least one ablation application element within the heart, a memory to store a map of the chamber of the heart and store a different, respective default ablation-parameter set for each different region of the chamber, and processing circuitry to segment the map of the chamber into the different regions, receive a user input indicative of commencement of an ablation procedure, identify, responsively to the tracked position, a region of the chamber with which the at least one ablation application element is in contact, retrieve the respective default ablation-parameter set assigned to the identified region, and apply the retrieved default ablation-parameter set in controlling the ablation procedure.

23 Claims, 9 Drawing Sheets

(56) References Cited

U.S. PATENT DOCUMENTS

| | | | |
|---|---|---|---|
| 2012/0029504 A1* | 2/2012 | Afonso | A61B 18/1492 606/34 |
| 2013/0231562 A1* | 9/2013 | Budzelaar | A61B 8/445 600/439 |
| 2014/0022250 A1* | 1/2014 | Mansi | G06T 7/12 345/420 |
| 2015/0065836 A1 | 3/2015 | Thakur et al. | |
| 2015/0289776 A1* | 10/2015 | Raz | A61B 5/04012 600/382 |
| 2015/0294082 A1 | 10/2015 | Passerini et al. | |
| 2018/0318013 A1 | 11/2018 | Mangual-Soto | |

* cited by examiner

CARDIAC MAP SEGMENTATION

FIELD OF THE INVENTION

The present invention relates to ablation systems, and in particular, to ablation parameters.

BACKGROUND

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

A number of systems for intracardiac ablation therapy are commercially available, such as the CARTO® 3 system offered by Biosense Webster Inc. (Irvine, Calif.). CARTO tracks the position and operating parameters of the distal end of the catheter and displays this information electronically on a three-dimensional (3D) anatomical map of the heart. CARTO enables the system operator to electronically tag locations that have been ablated on the map and thus tracks the progress of the procedure.

US Patent Publication 2015/0294082 of Passerini, et al., describes a method and system for image-based patient-specific guidance of cardiac arrhythmia therapies. A patient-specific anatomical heart model is generated from medical image data of a patient. A patient-specific cardiac electrophysiology model is generated based on the patient-specific anatomical heart model and electrophysiology measurements of the patient. One or more virtual electrophysiological interventions are performed using the patient-specific cardiac electrophysiology model. One or more pacing targets or ablation targets based on the one or more virtual electrophysiological interventions are displayed.

US Patent Publication 2015/0065836 of Thakur, et al., describes a system and method for mapping an anatomical structure includes sensing activation signals of physiological activity with a plurality of mapping electrodes disposed in or near the anatomical structure. Patterns among the sensed activation signals are identified based on a similarity measure generated between each unique pair of identified patterns which are classified into groups based on a correlation between the corresponding pairs of similarity measures. A characteristic representation is determined for each group of similarity measures and displayed as a summary plot of the characteristic representations.

U.S. Pat. No. 6,317,631 to Ben-Haim, et al., describes a method of modifying the force of contraction of at least a portion of a heart chamber, including providing a subject having a heart, comprising at least a portion having an activation, and applying a non-excitatory electric field having a given duration, at a delay after the activation, to the portion, which causes the force of contraction to be increased by at least 5%.

SUMMARY

There is provided in accordance with an embodiment of the present disclosure, a cardiac ablation system, including an ablation probe including at least one ablation application element configured to ablate tissue in a chamber of a heart of a living subject, a tracking module configured to track a position of the at least one ablation application element within the heart, a memory configured to store a map of the chamber of the heart and to store a different, respective default ablation-parameter set for each of a plurality of different regions of the chamber, and processing circuitry configured to segment the map of the chamber into the different regions, receive a user input indicative of commencement of an ablation procedure, identify, responsively to the tracked position, a region of the chamber with which the at least one ablation application element is in contact, responsively to the user input, retrieve the respective default ablation-parameter set assigned to the identified region, and apply the retrieved default ablation-parameter set in controlling the ablation procedure.

Further in accordance with an embodiment of the present disclosure the processing circuitry is configured to apply a segmented model of a heart chamber to the map of the chamber yielding a segmented map of the chamber.

Still further in accordance with an embodiment of the present disclosure the processing circuitry is configured to receive at least one user correction to a segmentation of the segmented map, and responsively to the received at least one user correction, amend the segmented map.

Additionally, in accordance with an embodiment of the present disclosure the processing circuitry is configured to receive a user markup of the map of the chamber dividing the map into the different regions, and responsively to the received user markup, segment the map of the chamber into the different regions.

Moreover, in accordance with an embodiment of the present disclosure the processing circuitry is configured to receive user-defined default ablation-parameter sets for each of the different regions, and responsively to a regional designation of each of the received user-defined default ablation-parameter sets, assign the user-defined default ablation-parameter sets to the different regions.

Further in accordance with an embodiment of the present disclosure the processing circuitry is configured to control ablation by the ablation probe of the tissue at the identified region the retrieved default ablation-parameter set.

Still further in accordance with an embodiment of the present disclosure the processing circuitry is configured to receive a user update to the retrieved default ablation-parameter set yielding an updated ablation-parameter set, and control ablation by the ablation probe of the tissue at the identified region the updated ablation-parameter set.

Additionally, in accordance with an embodiment of the present disclosure the processing circuitry is configured to assign a probe-specific default ablation-parameter set to each of the different regions for a plurality of different probe-types, and responsively to the user input, retrieve the probe-specific default ablation-parameter set assigned to the identified region for a probe-type of the ablation probe.

Moreover in accordance with an embodiment of the present disclosure the ablation probe includes a multiplicity of ablation application elements, and the processing circuitry is configured to identify, responsively to the tracked position, a first region of the chamber with which at least a first one of the multiplicity of ablation application elements is in contact, identify, responsively to the tracked position, a second region of the chamber with which at least a second one of the multiplicity of ablation application elements is in contact, retrieve the default ablation-parameter set assigned to the first region and the default ablation-parameter set assigned to the second region, and apply the retrieved default ablation-parameter set of the first and second region to perform the ablation procedure at the first and second region using the first one and the second one of the multiplicity of ablation application elements, respectively.

Further in accordance with an embodiment of the present disclosure the default ablation-parameter set for one region of the different regions includes any one or more of the following a tissue thickness of the one region, whether to track temperature during the ablation procedure, an ablation mode to use during the ablation procedure, an irrigation rate to use during the ablation procedure, a power level to apply during the ablation procedure, a force to apply during the ablation procedure, an ablation duration of the ablation procedure, an ablation index to use during the ablation procedure, a target power, and a target temperature.

Still further in accordance with an embodiment of the present disclosure the ablation mode is selected from any one or more of the following ablation index mode, controlling ablation power a measured temperature, applying an alternating current to the at least one ablation application element, applying a direct current to the at least one ablation application element, laser ablation, electroporation, cryoablation, radio-frequency power ablation.

There is also provided in accordance with another embodiment of the present disclosure, a cardiac ablation method, including tracking a position of at least one ablation application element of an ablation probe configured to ablate tissue in a chamber of a heart of a living subject, storing a map of the chamber of the heart, storing a different, respective default ablation-parameter set for each of a plurality of different regions of the chamber, segmenting the map of the chamber into the different regions, receiving a user input indicative of commencement of an ablation procedure, identifying, responsively to the tracked position, a region of the chamber with which the at least one ablation application element is in contact, responsively to the user input, retrieving the respective default ablation-parameter set assigned to the identified region, and applying the retrieved default ablation-parameter set in controlling the ablation procedure.

Additionally, in accordance with an embodiment of the present disclosure, the method includes applying a segmented model of a heart chamber to the map of the chamber yielding a segmented map of the chamber.

Moreover, in accordance with an embodiment of the present disclosure, the method includes receiving at least one user correction to a segmentation of the segmented map, and responsively to the receiving the at least one user correction, amending the segmented map.

Further in accordance with an embodiment of the present disclosure, the method includes receiving a user markup of the map of the chamber dividing the map into the different regions, and responsively to the receiving the user markup, segmenting the map of the chamber into the different regions.

Still further in accordance with an embodiment of the present disclosure, the method includes receiving user-defined default ablation-parameter sets for each of the different regions, and responsively to a regional designation of each of the received user-defined default ablation-parameter sets, assigning the user-defined default ablation-parameter sets to the different regions.

Additionally, in accordance with an embodiment of the present disclosure, the method includes controlling ablation by the ablation probe of the tissue at the identified region the retrieved default ablation-parameter set.

Moreover, in accordance with an embodiment of the present disclosure, the method includes receiving a user update to the retrieved default ablation-parameter set yielding an updated ablation-parameter set, and controlling ablation by the ablation probe of the tissue at the identified region the updated ablation-parameter set.

Further in accordance with an embodiment of the present disclosure, the method includes assigning a probe-specific default ablation-parameter set to each of the different regions for a plurality of different probe-types, and responsively to the user input, retrieving the probe-specific default ablation-parameter set assigned to the identified region for a probe-type of the ablation probe.

Still further in accordance with an embodiment of the present disclosure the ablation probe includes a multiplicity of ablation application elements, and the method further includes identifying, responsively to the tracked position, a first region of the chamber with which at least a first one of the multiplicity of ablation application elements is in contact, identifying, responsively to the tracked position, a second region of the chamber with which at least a second one of the multiplicity of ablation application elements is in contact, retrieving the default ablation-parameter set assigned to the first region and the default ablation-parameter set assigned to the second region, and applying the retrieved default ablation-parameter set of the first and second region to perform the ablation procedure at the first and second region using the first one and the second one of the multiplicity of ablation application elements, respectively.

Additionally in accordance with an embodiment of the present disclosure the default ablation-parameter set for one region of the different regions includes any one or more of the following a tissue thickness of the one region, whether to track temperature during the ablation procedure, an ablation mode to use during the ablation procedure, an irrigation rate to use during the ablation procedure, a power level to apply during the ablation procedure, a force to apply during the ablation procedure, an ablation duration of the ablation procedure, an ablation index to use during the ablation procedure, a target power, and a target temperature.

Moreover, in accordance with an embodiment of the present disclosure the ablation mode is selected from any one or more of the following ablation index mode, controlling ablation power a measured temperature, applying an alternating current to the at least one ablation application element, applying a direct current to the at least one ablation application element, laser ablation, electroporation, cryoablation, radio-frequency power ablation.

There is also provided in accordance with still another embodiment of the present disclosure, a software product, including a non-transient computer-readable medium in which program instructions are stored, which instructions, when read by a central processing unit (CPU), cause the CPU to track a position of at least one ablation application element of an ablation probe configured to ablate tissue in a chamber of a heart of a living subject, store a map of the chamber of the heart, store a different, respective default ablation-parameter set for each of a plurality of different regions of the chamber, segment the map of the chamber into the different regions, receive a user input indicative of commencement of an ablation procedure, identify, responsively to the tracked position, a region of the chamber with which the at least one ablation application element is in contact, responsively to the user input, retrieve the respective default ablation-parameter set assigned to the identified region, and apply the retrieved default ablation-parameter set in controlling the ablation procedure.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
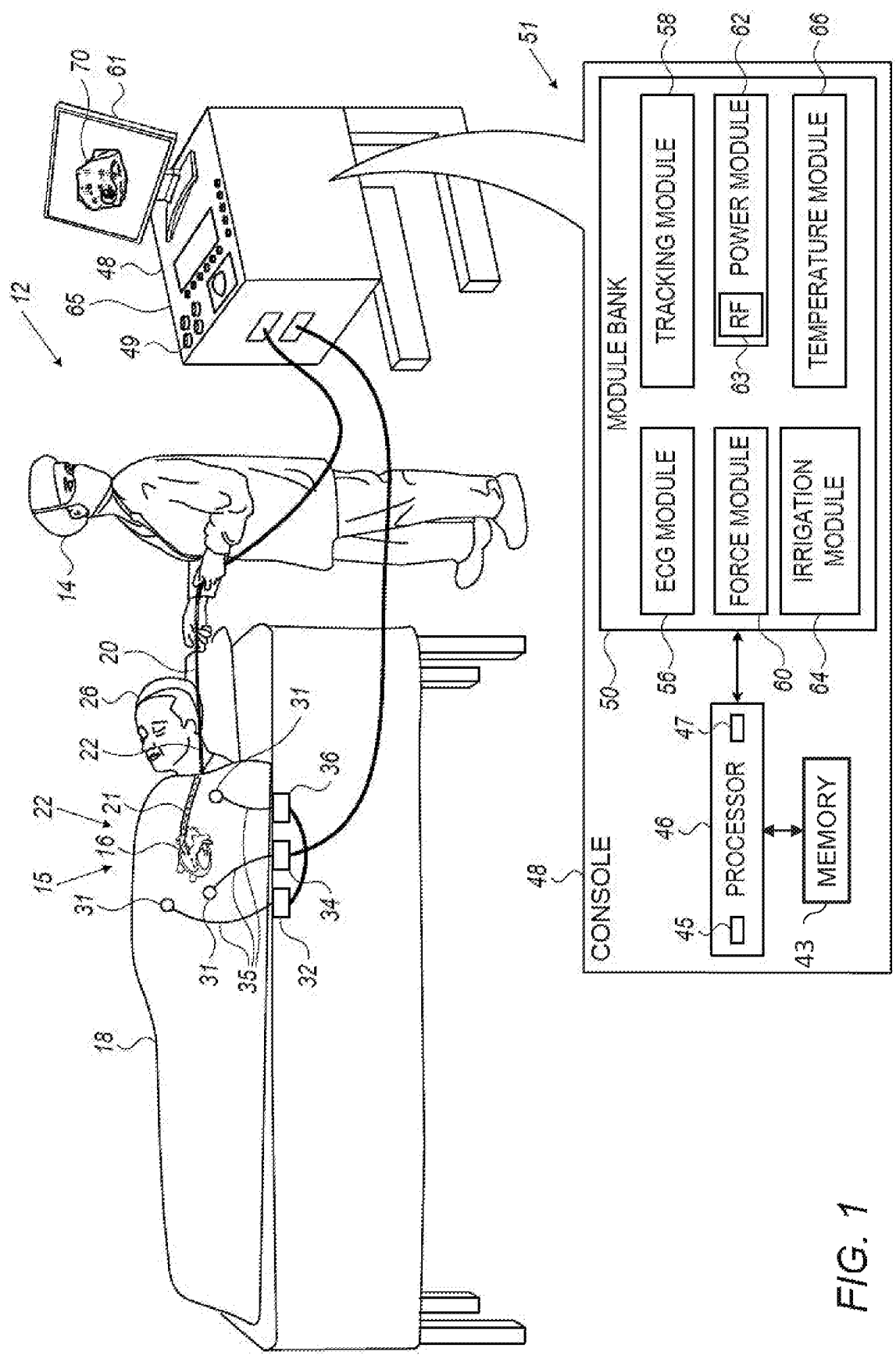
FIG. 1 a schematic illustration of an invasive medical procedure using an apparatus according to an embodiment of the present invention.

During an ablation procedure a physician may set ablation parameters such as power, ablation duration, irrigation rate of a cooling fluid, contact force between the ablation catheter and the tissue being ablated, by way of example only. In order to set the parameters, the physician has to mentally manage the necessary parameter settings without guidance from the ablation apparatus, and make the settings manually.

The parameter setting process is time-consuming, and requires physician decision making before, during, and after each ablation regarding medical issues as well as control of the ablation apparatus.

The process may lead to errors due to the number of decisions that need to be taken. Additionally, time is generally of the essence in cardiac procedures.

The above problems may be magnified as ablation equipment becomes more varied. For example, the catheter may be a focal ablation catheter or a balloon type catheter, each with its specific electrodes. In such circumstances, setting of ablation parameters, which may include taking into account the anatomy of the individual patient, becomes more onerous and error prone.

Embodiments of the present invention provide default ablation-parameter sets to be used in an ablation procedure according to a tracked position of an ablation probe. So, for example, if the ablation probe is contact with one region of heart tissue, a default ablation-parameter set for that region is retrieved for use with the ablation procedure in that region. When the ablation probe is contact with a second region of the heart tissue, a different ablation-parameter set for the second region is retrieved for use with the ablation procedure in that second region.

The physician may be provided with the option to amend one or more settings in the retrieved default ablation-parameter set prior to performing ablation with the ablation probe.

Prior to commencing the ablation procedure, a map of a chamber of a heart of a patient is acquired from an image of the heart (e.g., from a CT or MRI) or from a mapping performed using a mapping tool inserted into the heart chamber of the patient.

The map of the chamber of the heart may be segmented automatically by applying a segmented model of a heart chamber to the map of the chamber of the heart of the patient yielding a segmented map of the chamber of the heart of the patient. The segmented map may also include labels labelling the various regions of the heart, e.g., posterior wall, anterior wall etc.

The segmented map may be inspected by the physician and optionally corrected by the physician prior to use. In some embodiments, the segmented map may be used without prior inspection.

In other embodiments, the map of the chamber of the heart of the patient may be segmented based on user markup and labelling of the map provided by the physician using a suitable user interface.

Default ablation-parameter sets may be assigned to the various different regions of the segmented map according to the labels of the various regions. For example, a default ablation-parameter set for posterior wall is assigned to the region labelled posterior wall. Alternatively, the default ablation-parameter sets may be assigned to the different regions manually by the physician. In other embodiments, the default ablation-parameter sets may be assigned automatically by the system with the physician being given the option to inspect, and correct, the various automatically assigned settings.

The default ablation-parameter set for a region may include any one or more of the following: a tissue thickness of the region; whether to track temperature during the ablation procedure; an ablation mode to use during the ablation procedure; an irrigation rate to use during the ablation procedure; a power level to apply during the ablation procedure; a force to apply during the ablation procedure; an ablation duration of the ablation procedure; an ablation index (described in more detail with reference to FIG. 1) to use during the ablation procedure; a target power; and/or a target temperature, by way of example only.

The ablation mode may be selected from any one or more of the following: ablation index mode; controlling ablation power according to a measured temperature; applying an alternating current to the at least one ablation application element; applying a direct current to the at least one ablation application element; laser ablation; electroporation; cryoablation; and/or radio-frequency power ablation, by way of example only.

For example, lower power settings may be suggested for the posterior wall than the anterior wall because the posterior wall is near the esophagus which may be damaged by heat during the ablation. Similarly, performing ablation while adjusting ablation power according to a monitored tissue temperature may be suggested for the posterior wall whereas using ablation index may be suggested for the anterior wall. Other factors and examples are described in more detail with reference to the system description included below.

The default ablation-parameter sets may be probe-specific to take into account the different properties and capabilities of the different ablation probe-types. Therefore, when the default ablation-parameter set for a region is retrieved, the probe-specific default ablation-parameter set for that region may be retrieved. For example, a focal catheter may default to an ablation index threshold or temperature guided ablation settings for the region, while for a balloon catheter the power settings of the various electrodes may be set based on the region as well as the current location of each electrode within that region.

In some embodiments, two or more default ablation-parameter sets may be retrieved a multi-electrode catheter. For example, if some of the electrodes of the multi-electrode catheter are in contact with a first region of the tissue but other electrodes of the multi-electrode catheter are in contact with a second region of the tissue, the default ablation-parameter set for the multi-electrode catheter of the first region and the default ablation-parameter set for the multi-electrode catheter of the second region are retrieved for use in ablation with the electrodes in contact with the tissue of the first region and the second region, respectively. The multi-electrode catheter described herein may be generalized to a multi-ablation application element catheter using any suitable ablation method, for example, but not limited to, laser ablation, electroporation, and/or cryoablation. Similarly, the probes described above may utilize any suitable ablation method, for example, but not limited to, laser ablation, electroporation, cryoablation, and/or radio-frequency ablation.

The default ablation-parameter sets may also be tailored for different ablation modes being used by the ablation probes. For example, one default ablation-parameter set may be retrieved if the probe is using ablation index and another default ablation-parameter set may be retrieved if the probe is using another ablation mode. Alternatively, the default ablation-parameter set for each region may be a global parameter set, which includes the default ablation-parameters for a multiplicity of ablation modes and/or probes so that the relevant default ablation-parameters may be extracted from global parameter set according to the ablation mode and/or probe-type being used.

While a physician may override the default settings, embodiments of the present invention automatically add an extra layer of safety without the need for manual intervention.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
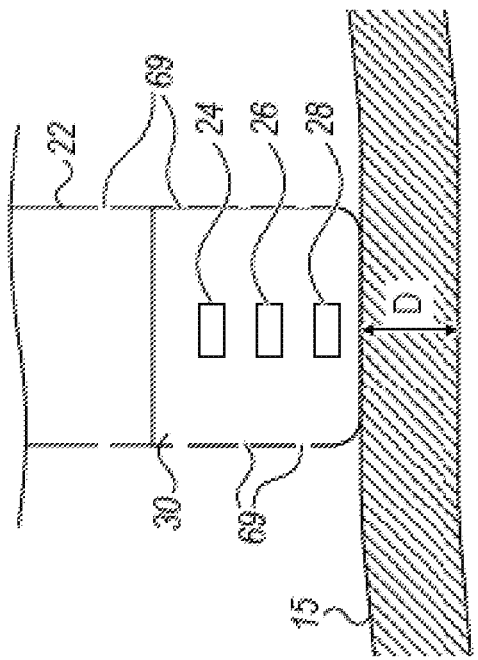
FIG. 2 is a schematic illustration of a distal end of a probe used in the apparatus of FIG. 1 according to an embodiment of the present invention.

Reference is now made to FIG. 1, which is a schematic illustration of an invasive medical procedure using a cardiac ablation apparatus 12 according to an embodiment of the present invention. Reference is also made to FIG. 2, which is a schematic illustration of a distal end 22 of a probe 20 used in the apparatus 12 according to an embodiment of the present invention. The procedure is performed by a physician 14, and in the description hereinbelow the procedure is assumed to comprise an ablation of a portion of tissue 15 of a myocardium 16 of the heart of a human patient 18.

In order to perform the procedure, the physician 14 inserts the probe 20 into a sheath 21 that has been pre-positioned in a lumen of the patient 18 so that the probe 20 is inserted into a chamber of the heart. The sheath 21 is positioned so that the distal end 22 of the probe 20 enters the heart of the patient 18. The distal end 22 comprises a position sensor 24 that enables the location and orientation of the distal end 22 to be tracked, a force sensor 26 that measures the force applied by the distal end 22 when it contacts the myocardium 16, and one or more temperature sensors 28 that measure the temperature at respective locations of the distal end 22. The distal end 22 also comprises one or more electrodes 30 which are used to apply radiofrequency power to the myocardium 16 in the chamber so as to ablate the myocardium 16. The electrode(s) 30 may also be used to acquire electropotentials from the myocardium 16.

The apparatus 12 is controlled by a system processor 46, which is located in an operating console 48 of the apparatus. The operating console 48 comprises controls of at least one user input device 49 which are used by the physician 14 to communicate with the processor 46. The software for processor 46 may be downloaded to the processor 46 in electronic form, over a network, for example. Alternatively, or additionally, the software may be provided on non-transitory tangible media, such as optical, magnetic, or electronic storage media.

The processor 46 may comprise real-time noise reduction circuitry 45, typically configured as a field programmable gate array (FPGA), followed by an analog-to-digital (A/D) signal conversion integrated circuit 47. The processor 46 can pass the signal from the A/D signal conversion integrated circuit 47 to another processor and/or can be programmed to perform at least one algorithm disclosed herein, the algorithm comprising steps described hereinbelow. The processor 46 uses the noise reduction circuitry 45 and the A/D signal conversion integrated circuit 47, as well as features of modules which are described in more detail below, in order to perform the algorithm. A memory 43 is configured to store data used by the processor 46.

In order to operate the apparatus 12, the algorithm of the processor 46 communicates with a module bank 50, which has a number of modules used by the processor 46 to operate the apparatus 12. Thus, the module bank 50 comprises an electrocardiograph (ECG) module 56 coupled to receive signals from body surface electrodes 31 and/or electrodes 30, in order to provide the ECG signals to the processor 46. The body surface electrodes 31 and/or the electrode(s) 30 are configured for application to a body of a subject (e.g., the patient 18) and configured to output signals in response to electrical activity of a heart of the subject. The electrode(s) 30 is applied to the heart of the body via the probe 20. The module bank 50 also includes a tracking module 58 which receives and analyzes signals from the position sensor 24, and which uses the signal analysis to generate a location and an orientation of the distal end 22. In some embodiments the position sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing the position sensor 24. The radiators 32, 34, 36 are positioned in proximity to the myocardium 16, and are configured to radiate alternating magnetic fields into a region in proximity to the myocardium 16. A plurality of wire connections 35 link the operating console 48 with body the surface electrodes 31 and other components (such as the radiators 32, 34, 36 and the sensor 24) to enable the tracking module 58 to measure location and orientation coordinates of the probe 20. In some embodiments, the tracking module 58 is configured to compute a relative location and a relative orientation of the probe 20 with respect to the heart. Magnetic location and orientation tracking is described in U.S. Pat. Nos. 7,756,576 and 7,536,218, which are hereby incorporated by reference. The CARTO system produced by Biosense Webster, of 33 Technology Drive, Irvine, Calif. 92618 USA, uses such a magnetic tracking system. The tracking module 58 is not limited to using magnetic based location and orientation tracking. Any suitable location and orientation tracking can be used, such as impedance-based or image-based tracking.

The apparatus 12 may receive image data from an external imaging modality, such as an MRI unit, CT unit or the like and includes image processors that can be incorporated in or invoked by the processor 46 for generating and displaying images. The image data may be registered with the tracking module 58 and a user interface screen 70 combining the received data and positions of the probe 20 may be displayed to the physician 14 on a display 61. For example, the track of the distal end 22 of the probe 20 may be shown on a three-dimensional (3D) representation of the heart of patient 18 that is displayed on the display 61. In some embodiments, the 3D representation of the heart may be at least partially computed based on mapping performed by the probe 20.

The electrode(s) 30 and the body surface electrodes 31 may be used to measure tissue impedance at the ablation site as taught in U.S. Pat. No. 7,536,218, issued to Govari et al., which is herein incorporated by reference.

The module bank 50 also comprises a force module 60, a power module 62, an irrigation module 64, and a temperature module 66. The functions of these modules are explained below. The modules in the module bank 50, and the processor 46, are herein termed processing circuitry 51.

The force module 60 receives signals from the force sensor 26, and from the signals generates a magnitude of the contact force, herein assumed to be measured in grams, exerted by the distal end 22 on the tissue 15. In some embodiments the force sensor 26 is configured so that the signals it provides to the force module 60 enable the force module 60 to evaluate a direction of the force exerted by the distal end 22 on the tissue 15.

The power module 62 comprises a radiofrequency (RF) signal generator 63 which generates the radiofrequency power to be applied by the electrode(s) 30 to ablate the tissue 15 of the myocardium 16. The processor 46 and the power module 62 are able to adjust a power level, herein assumed to be measured in Watts, delivered by the electrode(s) 30, as well as a length of time, measured in seconds, during which the power is delivered.

The irrigation module 64 controls a rate of flow, herein assumed to be measured in mL/min, of irrigation fluid, typically normal saline solution, supplied to the distal end 22 by a pump 65 disposed in the operating console 48. The probe 20 includes an irrigation channel through which to irrigate the myocardium 16. The irrigation fluid is expelled from irrigation holes 69 in the distal end 22. The pump 65 is configured to selectively pump the irrigation fluid into the irrigation channel at an idle rate and at one or more one non-idle rates (higher than the idle rate) according to a status of the ablation procedure.

The temperature module 66 receives a temperature signal provided by the temperature sensor 28 (or by each temperature sensor 28). The temperature signal is indicative of a temperature of the myocardium at a plurality of different times. The temperature module 66 determines the temperatures registered by each of the sensors 28. Typically, in the case of multiple sensors 28 the temperature module 66 determines a mean temperature of the distal end 22. Additionally, in the case of multiple sensors, the temperature module 66 may produce a map of the temperature distribution of the distal end 22.

Ablation may be performed according to any suitable ablation mode, for example, but not limited to, ablation index mode, or where ablation power and/or the irrigation rate is modified according to temperature or rate of change of temperature measured by the temperature sensor 28 or another temperature sensor disposed in any suitable location. Both these modes are described in some more detail below. The apparatus 12 may also be modified to perform non-RF ablation or another type of ablation in addition to RF-ablation, for example, but not limited to, laser ablation, electroporation, and/or cryoablation.

As is known in the art, an ablation index is a function, having a value that changes as ablation proceeds, and provides an estimate of the size of a lesion produced by the ablation of a tissue of known type. The estimate provided by the index depends on the values of the contact force CF and power P measured during the ablation, as well as on the period of time of the ablation. Ablation indices are described in an article entitled "Ablation Index-guided Pulmonary Vein Isolation for Atrial Fibrillation may Improve Clinical Outcomes in Comparison to Contact Force-guided Ablation" to Hussein et al., presented at the 2016 Heart Rhythm Congress, and in U.S. Patent Application 2017/0014181 to Bar-Tal et al. Both documents are incorporated herein by reference.

Equation (1) below gives an expression for an ablation index:

$$D = (C\int_0^t CF^\alpha(\tau) P^\beta(\tau) d\tau = \text{Ablation Index} \quad (1)$$

where C is a constant having a value depending on the type of tissue being ablated; in one embodiment C has an approximate value of 0.002, $\alpha$ is an exponent having a value typically in the range 0.6-0.8, $\beta$ is an exponent having a value typically in the range 1.4-1.8, $\delta$ is an exponent having an approximate value of 0.35, and D is an estimate of the depth of a lesion achieved by ablating for a time t, with instantaneous contact force $CF(\tau)$ and instantaneous power $P(\tau)$, and where T represents a time variable.

If the contact force and the power are assumed to be constant, having respective values $\overline{CF}$ and $\overline{P}$ during an ablation procedure that is to take a time t, then equation (1) may be rewritten as equation (2):

$$D = (C\overline{CF}^\alpha \overline{P}^\beta t)^\delta \quad (2)$$

If the value of the left side of equation (2), tissue thickness D, is known (from estimates, scans, or other calculations), the processor 46 may thus use the right side of equation (2) to provide to the physician 14 recommended values of power P and time t for ablation using the measured value of force CF and an estimate of C. The physician 14 may select one of the recommended values of power P and time t to ablate tissue 15, and conclude the ablation of tissue 15 with these values.

The ablation index acts as an aid to the physician in deciding values of parameters, such as power and time period of ablation, to be used during an ablation procedure.

Pending patent application Ser. No. 16/196,255 of Govari, et al., filed on 20 Nov. 2018 describes adjusting power and irrigation according to a measured temperature and rate of change of temperature. An example function for calculating the irrigation rate and the change in power for each cycle of a plurality of cycles now follows.

New irrigation rate (flow)=currentFlow+deltaFlow
(Temp)+deltaFlow(Power)   (Equation 1), where currentFlow is the current irrigation rate, deltaFlow(Temp)=$At^*\Delta T+Bt^*$TempSlope+$Ct^*\int\Delta T+Dt^*$avg($\Delta T$), and deltaFlow(Power)=$Ap^*\Delta P+Bp^*$PowerSlope+$Cp^*\int\Delta P+Dp^*$avg($\Delta P$), $\Delta T$ is the difference between TargetTemp (the target temperature) and Temp (the sampled temperature, which could be an average of several sample cycles), TempSlope is equal to the rate of change of the sampled temperature and could be computed from averaged samples, $\int\Delta T$ is an integral of $\Delta T$ and the integral time range may vary, avg($\Delta T$) is an average of $\Delta T$, At is a tuning parameter for $\Delta T$, Bt is a tuning parameter for TempSlope, Ct is a tuning parameter for $\int\Delta T$, Dt is a tuning parameter for avg($\Delta T$), $\Delta P$ is the difference between TargetPower (the target power) and Power (sampled power, which could be an average of several sample cycles), PowerSlope is the rate of change of the sampled power and could be computed from averaged samples, $\int\Delta P$ is an integral of $\Delta P$ and the integral time range may vary, avg($\Delta P$) is an average of $\Delta P$, Ap is a tuning parameter for $\Delta P$, Bp is a tuning parameter for PowerSlope, Cp is a tuning parameter for $\int\Delta P$, Dp is a tuning parameter for avg($\Delta P$).

The initial irrigation rate (flow) may be calculated as follows:

Flow=FlowLow+(FlowHigh−FlowLow)/(Power-
High−PowerLow)*(TargetPower−PowerLow)   (Equation 2), where FlowLow is the lowest irrigation rate provided by the system, FlowHigh is the highest irrigation rate provided by the system, PowerLow is the lowest power provided by the system, and PowerHigh is the highest power provided by the system.

Example ranges and values for the various parameter are given below. However, it should be noted that the values may be any suitable value even outside of the ranges given below.

| Parameter | Example range | Example value |
| --- | --- | --- |
| $\int\Delta T$ | 0.5 sec to 2 sec | 1 sec |
| Avg($\Delta T$) | 1 sec to 5 sec | 2 sec |
| At | −0.9 to −0.1 | −0.5 |
| Bt | −0.9 to −0.1 | −0.3 |
| Ct | 0 to 0.1 | 0.015 |
| Dt | −0.9 to 0 | −0.05 |
| $\int\Delta P$ | 0.5 sec to 2 sec | 1 sec |
| Avg($\Delta P$) | 1 sec to 5 sec | 2 sec |
| Ap | 0.1 to 0.9 | 0.3 |
| Bp | 0.1 to 0.9 | 0.2 |
| Cp | −0.1 to 0 | 0 |
| Dp | 0 to 0.9 | 0 |

The above example ranges and values assume that $\Delta T$ is equal to TargetTemp (the target temperature) less Temp (the sampled temperature) and $\Delta P$ is TargetPower (the target power) less Power (the sampled power). The example ranges and values given above for the integrals refer to an example upper limit for the integration with the lower limit of integral being 0 seconds. The example ranges and values for Avg ($\Delta T$) and Avg($\Delta P$) refer to an example sampling time range for computing the average.

It should be noted that the parameters may be floating-point numbers and any of the parameters may be optionally averaged over a time period which may vary. The new irrigation rate could be a floating-point number with a limited range.

In some embodiments ablation power may be varied so that a target temperature as measured by the temperature sensor(s) is maintained. Varying different ablation parameters according to a measured temperature may be termed "temperature guided ablation".

The description below with reference to FIGS. 3-11 describes various exemplary methods for providing default ablation-parameter sets for use in an ablation procedure. The ablation procedure may be performed using the apparatus 12 and the probe 20 as described above with reference to FIGS. 1 and 2 or using the apparatus 12 with various modifications to the probe 20 and the operating console 48, for example, using different type of ablation probes including one or more ablation electrodes, or using different ablation methods, in addition to, or instead of, RF ablation. The addition ablation methods may include laser ablation, electroporation, and/or cryoablation, by way of example only. The ablation probe 20 may include at least one ablation application element configured to ablate tissue 15 in a chamber of the heart of the living subject (e.g., the patient 18). The one or more ablation application elements may include, ablation electrodes, laser apparatus, and/or refrigerant tubing, by way of example only. The ablation probe 20 may optionally include one or more of the following: a force sensor, a temperature sensor, a position sensor, and an irrigation system, as described above with reference to FIGS. 1 and 2. In other embodiments, the ablation probe 20 may include other sensors in addition to, or instead of, the sensors described above with reference to FIGS. 1 and 2. In some embodiments, the ablation probe 20 may not include an irrigation system.

Figure 3:
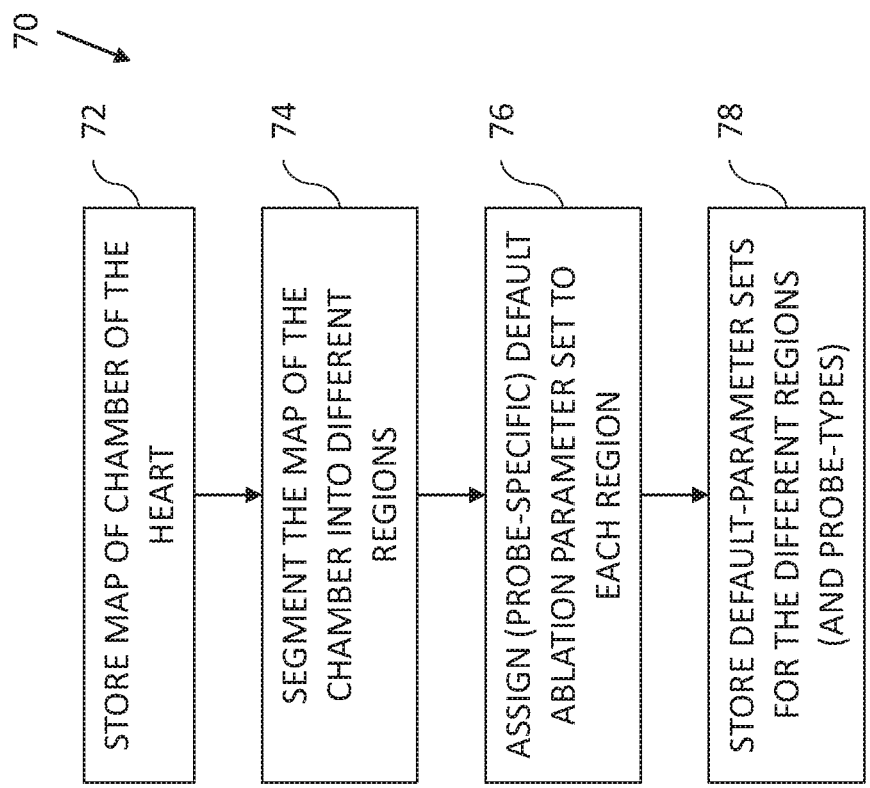
FIG. 3 is a flowchart including exemplary steps in a preparatory method for use with the apparatus of FIG. 1.

Reference is now made to FIG. 3, which is a flowchart 70 including exemplary steps in a preparatory method for use with the apparatus 12 of FIG. 1.

The processor 46 is configured to store (block 72) a map of the chamber of the heart in the memory 43 (FIG. 1). The map may be derived from a CT, MRI or other imaging technique or from a mapping provided using a mapping probe inside the chamber of the heart.

The processor 46 is configured to segment (block 74) the map of the chamber into different regions. Segmenting the map may be performed automatically, semi-automatically, or manually. Segmenting the map is described in more detail with reference to FIGS. 4-7.

The processor 46 is configured to assign (block 76) a default ablation-parameter set to each of the different regions. In some embodiments, each default ablation-parameter set may include default ablation-parameters for different probe types and/or different ablation modes being used by the ablation probe 20. In other embodiments, the processor 46 is configured to assign a probe-specific default ablation-parameter set to each of the different regions for a plurality of different probe-types. The default ablation-parameter sets may also be tailored for different ablation modes being used by the ablation probes. For example, one default ablation-parameter set may be retrieved if the probe is using ablation index and another default ablation-parameter set may be retrieved if the probe is using another ablation mode. Assigning the default ablation-parameter sets to the different regions is described in more detail with reference to FIG. 6.

The default ablation-parameter set for one region of the different regions may include any one or more of the following, by way of example only: a tissue thickness of the region; whether to track temperature during the ablation procedure; an ablation mode to use during the ablation procedure; an irrigation rate to use during the ablation procedure; a power level to apply during the ablation procedure; a force to apply during the ablation procedure; an ablation duration of the ablation procedure; an ablation index to use during the ablation procedure; a target power; and/or a target temperature.

The ablation mode may be selected from any one or more of the following, by way of example only: ablation index mode; controlling ablation power according to a measured temperature; applying an alternating current to the at least one ablation application element; applying a direct current to the at least one ablation application element; laser ablation; electroporation; cryoablation; and/or radio-frequency power ablation.

By way of example, ablation power applied near the posterior wall may be adjusted according to a measured temperature, either measured by the probe or using a sensor disposed near the esophagus. Therefore, a temperature driven ablation mode may be more suitable to the posterior wall whereas other ablation methods, e.g., ablation index, may be used in other regions of the chamber. By way of another example, ablation of appendages should be avoided as much as possible so power or the ablation index in that region may be set to a low value. By way of another example, ablation index values may be set to be higher for the anterior wall and lower for posterior wall. In general, the ablation index values may be set according to the estimated or actual thickness of tissue in the respective regions. Irrigation rate may also be set to a higher value for the posterior wall as compared to other regions, by way of example only. In general, ablation technique may depend on the region, so that the ablation mode which is most effective for a particular region is included in the default ablation-parameter set for that region.

For example, different default setting for the posterior wall, anterior wall and roof regions may be as follows:

Posterior wall—90 W ablation power 90 W, 4 seconds ablation duration, 2 g or above contact force;

Anterior wall—35 W ablation power, 550 units ablation index threshold, 15 ml per second irrigation rate, and 5 g or above contact force; and Roof—45 W ablation power, 450 units ablation index threshold, 15 ml per second irrigation rate, 5 g or above contact force.

The default ablation-parameters may be tailored as described above for different probe types, as some probes may be able to perform a given ablation mode (e.g., temperature guided ablation) whereas others cannot. Some probes may include elements (e.g., irrigation systems, lasers, or refrigerant tubing) whereas other may not.

The default ablation-parameters for multi-ablation application elements (e.g., a balloon catheter with multiple electrodes) may provide different default settings for different ones of the ablation application elements. In some embodiments, the default settings for the different ablation application elements may include different ablation application elements performing ablation with different ablation modes. A further example is provided with reference to FIG. 11.

The processor 46 is configured to store (block 78), in the memory 43, a different, respective default ablation-parameter set for each of the plurality of different regions of the chamber (and optionally for each probe-type) providing links between the default ablation-parameter sets and the regions (and probe-types).

Figure 4:
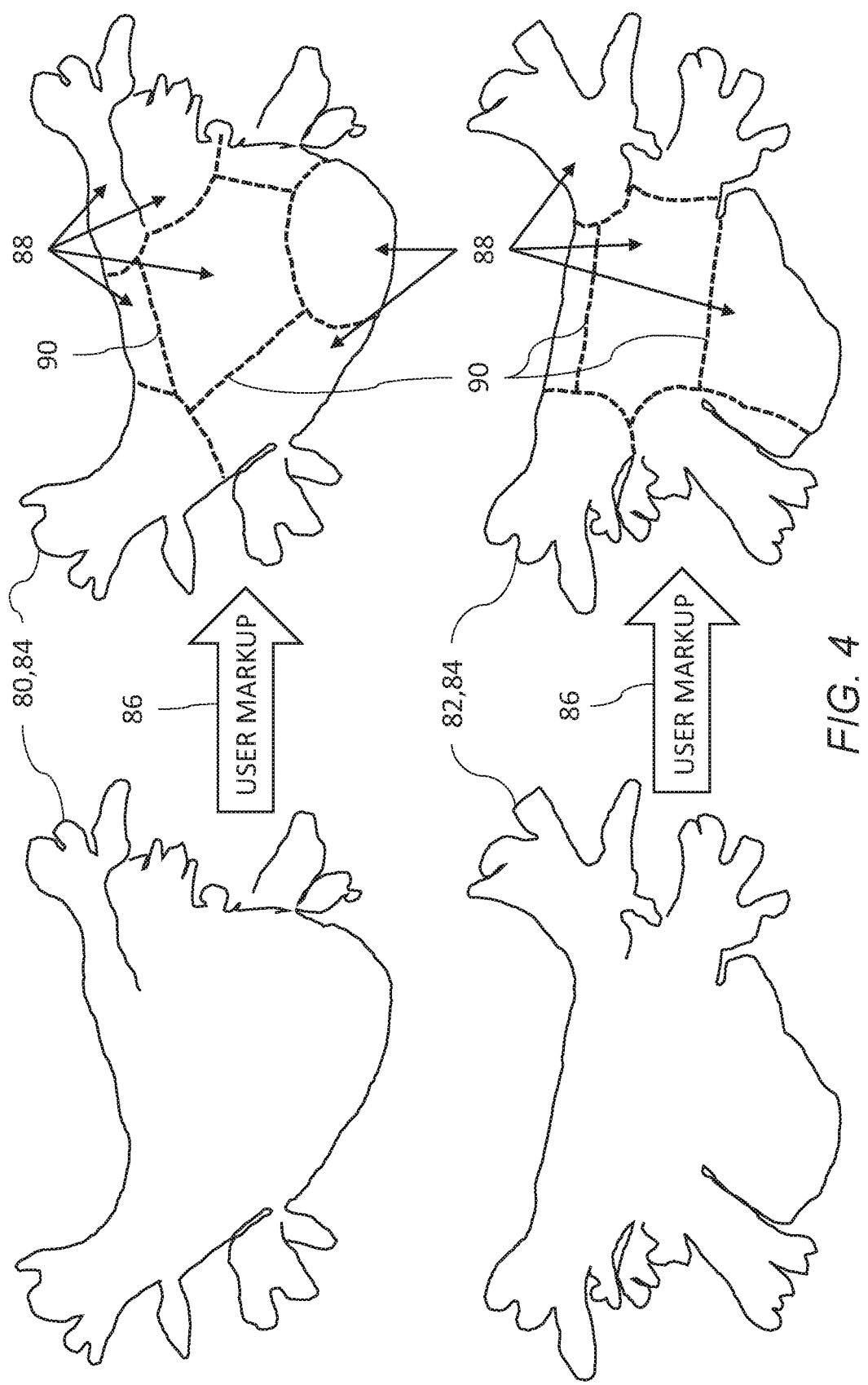
FIG. 4 is a schematic illustration of map segmentation for use with the apparatus of FIG. 1.

Reference is now made to FIG. 4, which is a schematic illustration of map segmentation for use with the apparatus 12 of FIG. 1. FIG. 4 shows an anterior view 80 and a posterior view 82 of a map 84 of a chamber of a heart before and after being divided into different regions 88 (only some labeled for the sake of simplicity). The anterior view 80 and posterior view 82 may be rendered for display by the processor 46 on to the display 61 (FIG. 1) or on to any other suitable display. The anterior view 80 and the posterior view 82 of the map 84 may be rendered as two separate two-dimensional (2D) images, or as part of a rotatable three-dimensional (3D) image which includes both the anterior view 80 and the posterior view 82. The processor 46 receives user markup 86 via the input device 49 (FIG. 1) and updates the map 84 with the user markup 86. The user markup 86 divides the map 84 into different regions 88 with regional boundaries 90 (only some labeled for the sake of simplicity).

Figure 5:
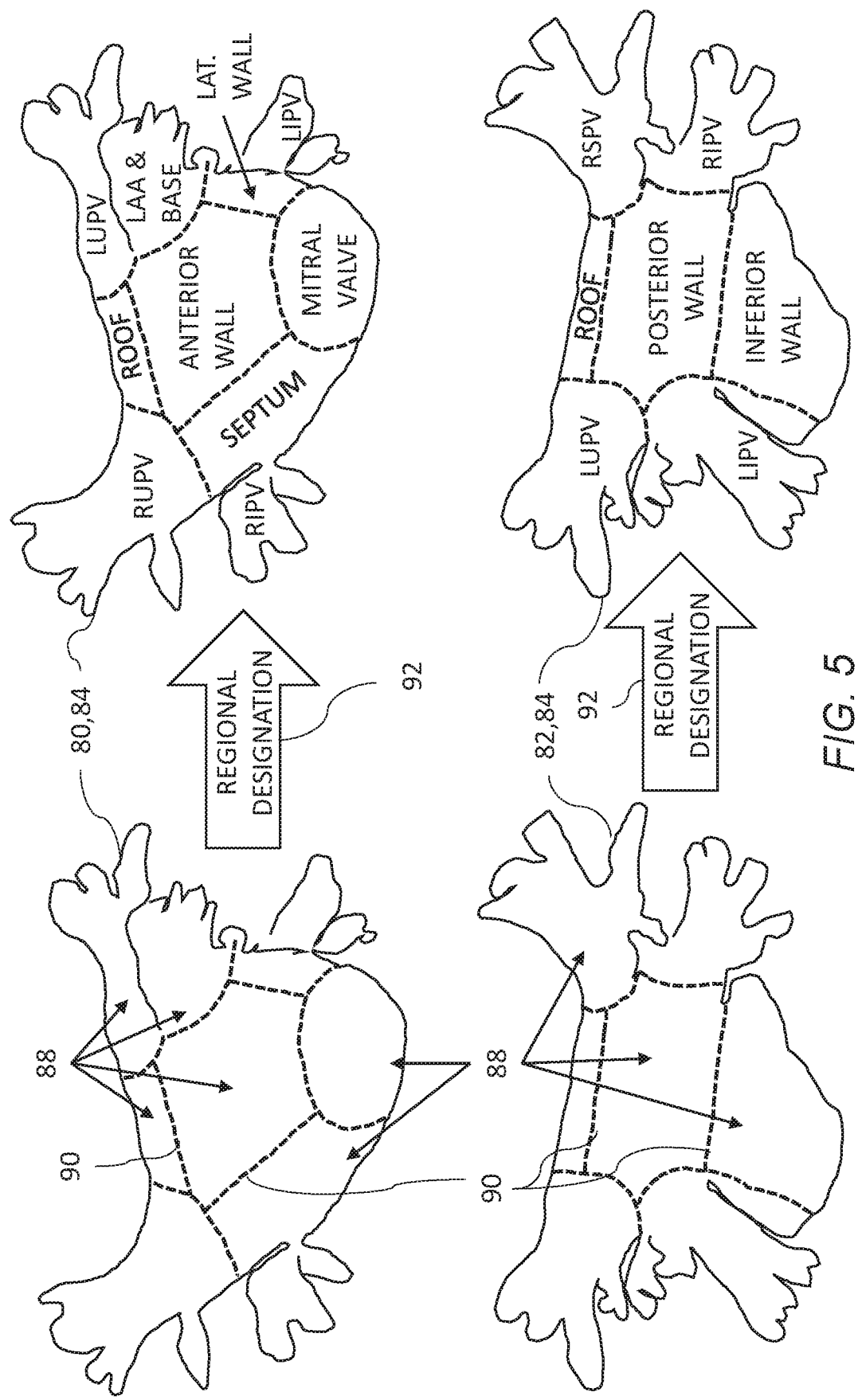
FIG. 5 is a schematic illustration of regional designation for use with the apparatus of FIG. 1.

Reference is now made to FIG. 5, which is a schematic illustration of regional designation for use with the apparatus 12 of FIG. 1. The segmented map 84 is then rendered for display by the processor 46 on to the display 61. The physician 14 (FIG. 1) may then add labels (e.g., roof, septum, mitral valve, etc.) providing a regional designation 92 to each of the regions 88 using the input device 49. The labels may be selected from a pre-populated list (e.g., pull-down list) and/or based on freeform text. The regions 88 listed in FIG. 5 are by way of example only, for a left atrium. The chamber may be divided up in to more, or less, regions 88 than the number of regions 88 shown in FIG. 5. FIGS. 4 and 5 have been described with reference to the left atrium. The method may also be implemented for any suitable heart chamber.

Figure 6:
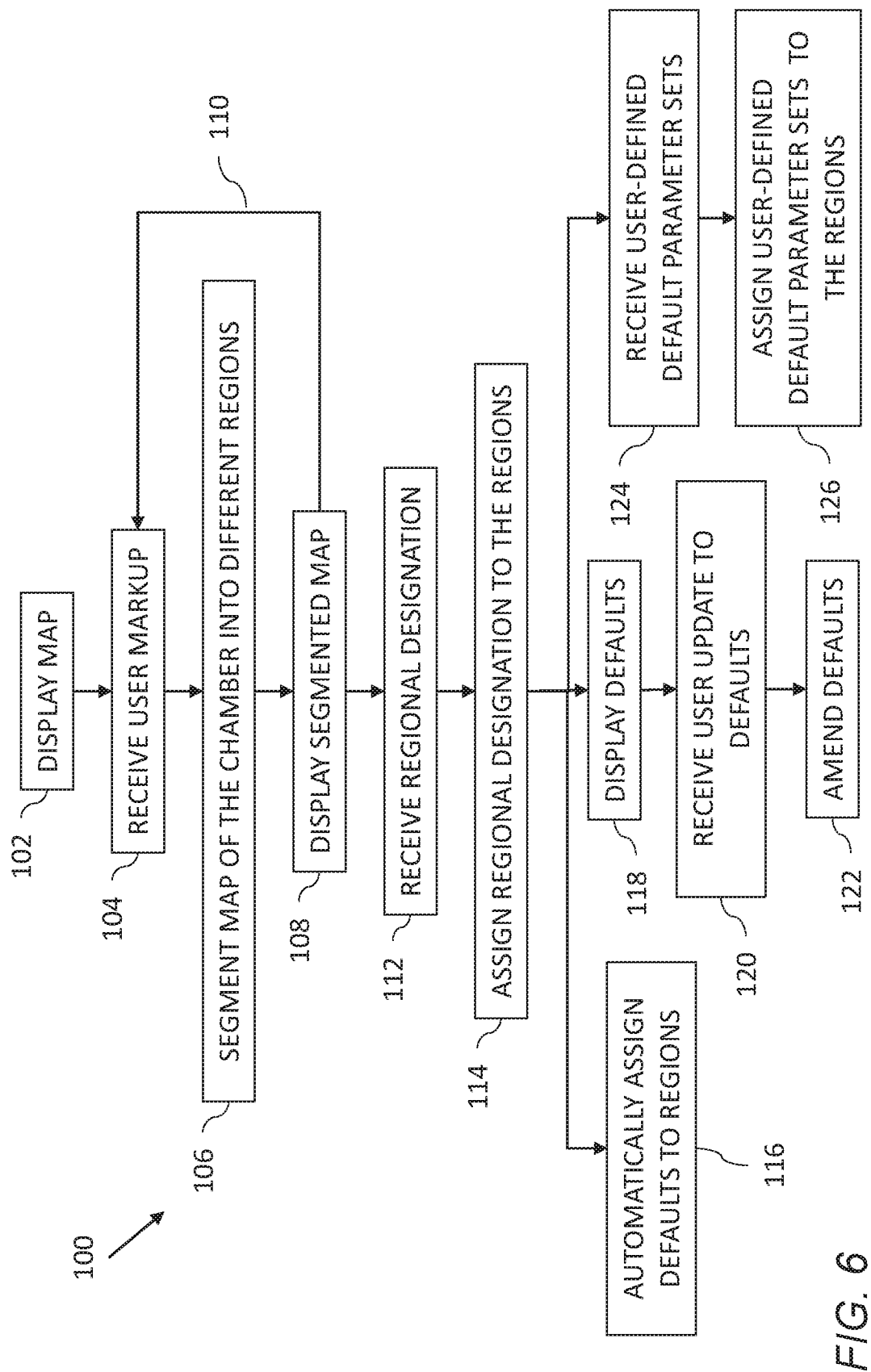
FIG. 6 is a flowchart including exemplary steps in a segmentation and regional designation method for use with the apparatus of FIG. 1.

Reference is now made to FIG. 6, which is a flowchart 100 including exemplary steps in a segmentation and regional designation method for use with the apparatus 12 of FIG. 1.

The processor 46 (FIG. 1) is configured to display (block 102) the map 84 on the display 61 (FIG. 1). The processor 46 is configured to receive (block 104), via the input device 49 (FIG. 1), the user markup 86 (FIG. 4) of the map 84 of the chamber dividing the map 84 into the different regions 88 (FIGS. 4 and 5). The processor 46 is configured to segment (block 106) the map 84 of the chamber into the different regions 88 responsively to the received user markup 86. The processor 46 is configured to display (block 108) the segmented map 84. If the map needs correcting the physician 14 may re-enter (arrow 110) corrected markup at the step of block 104. The processor 46 is configured to receive (block 112) the regional designation 92 (FIG. 5) of the different regions 88 of the map 84 designated by the physician 14. The processor 46 is configured to assign (block 114) the regional designation 92 to the regions 88 of the map 84.

Default ablation-parameters may be assigned to each of the regions 88 automatically, semi-automatically, or manually, as will now be described below.

In the automatic mode, the processor 46 is configured to automatically assign (block 116) default ablation-parameter sets to the regions 88 based on the regional designation 92 of each of the regions 88. For example, a previously stored default ablation-parameter set for the septum may be assigned to the septum region or a previously stored default ablation-parameter set for the LUPV region for a balloon catheter may be assigned to the LUPV region for use with a balloon catheter.

In the semi-automatic mode, the processor 46 is configured to display (block 118), to the display 61, the default ablation-parameter sets that have been automatically assigned to the regions 88 based on the regional designation 92 of each of the regions 88 as described with reference to the step of block 116. The physician 14 may then review the automatically assigned default ablation-parameter sets and update the default ablation-parameter sets using the input device 49. The processor 46 is configured to receive (block 120) the user update to the default ablation-parameter sets and amend (block 122) the default ablation-parameter sets according to the user update.

In the manual mode, the processor 46 is configured to receive (block 124) user-defined default ablation-parameter sets for each of the different regions 88 defined by the physician 14. The processor 46 is configured, responsively to a regional designation of each of the received user-defined default ablation-parameter sets, to assign the user-defined default ablation-parameter sets to the different regions 88.

Figure 7:
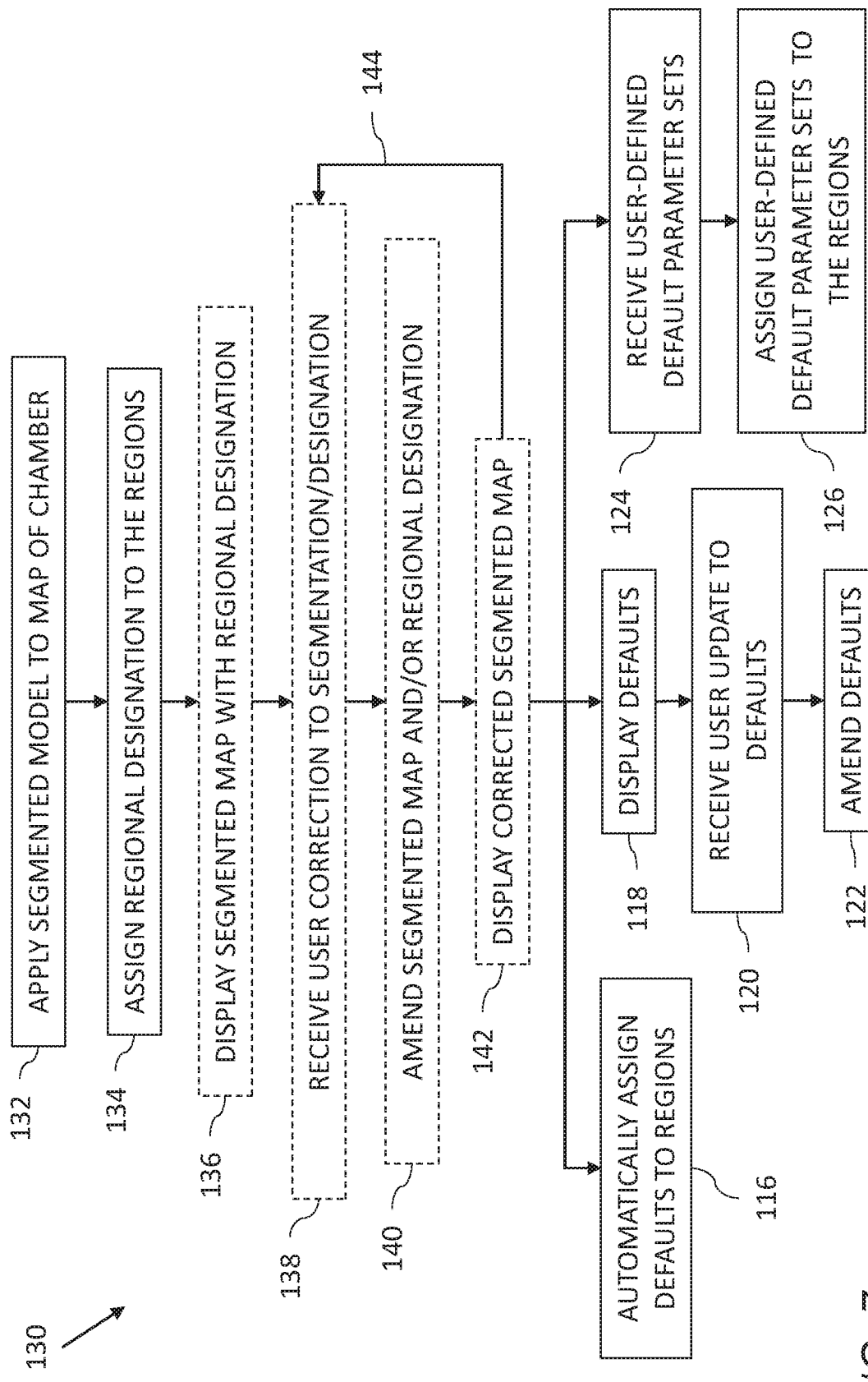
FIG. 7 is a flowchart including exemplary steps in an alternative segmentation and regional designation method for use with the apparatus of FIG. 1.

Reference is now made to FIG. 7, which is a flowchart 130 including exemplary steps in an alternative segmentation and regional designation method for use with the apparatus 12 of FIG. 1. FIG. 7 describes an automatic and semi-automatic method for segmenting the map 84 (FIGS. 4 and 5) based on a segmented model of a heart chamber. The processor 46 (FIG. 1) is configured to apply (block 132) a segmented model of a heart chamber to the map 84 of the chamber yielding a segmented map 84 of the chamber. The segmented model typically includes a segmented and labelled heart-chamber map previously prepared by a medical professional or based on collating previous segmented and labeled heart-chamber maps prepared by one or more medical professionals. The processor 46 may use image processing techniques including scaling the model vertically and horizontally and optionally moving a perimeter of the heart chamber model until the model matches the map 84. The processor 46 then applies the regional boundaries of the model to the map 84 yielding the segmented map 84 of the chamber. The processor 46 is configured to apply (block 134) the regional designation of the regions included in the model to the corresponding regions 88 of the map 84.

In accordance with some embodiments, the processor 46 is optionally configured to display (block 136) the segmented map 84 with the regional designation. The physician 14 may then inspect the map 84 to determine if corrections to the regional boundaries 90 and/or the regional designation 92 are required. The processor 46 is configured to receive (block 138), from the input device 49, at least one user correction to the segmentation and/or the regional designation 92. The processor 46 is configured to amend (block 140) the segmentation of the map 84 and/or the regional designation 92 responsively to the user correction(s). The processor 46 is configured to display (block 142) the corrected segmented map 84. The steps of blocks 138-142 may be repeated (arrow 144) to provide for subsequent user corrections.

Default ablation-parameters may be assigned to each of the regions 88 automatically, semi-automatically, or manually, as described above with reference to the steps of blocks 116-126 of FIG. 6.

Figure 8:
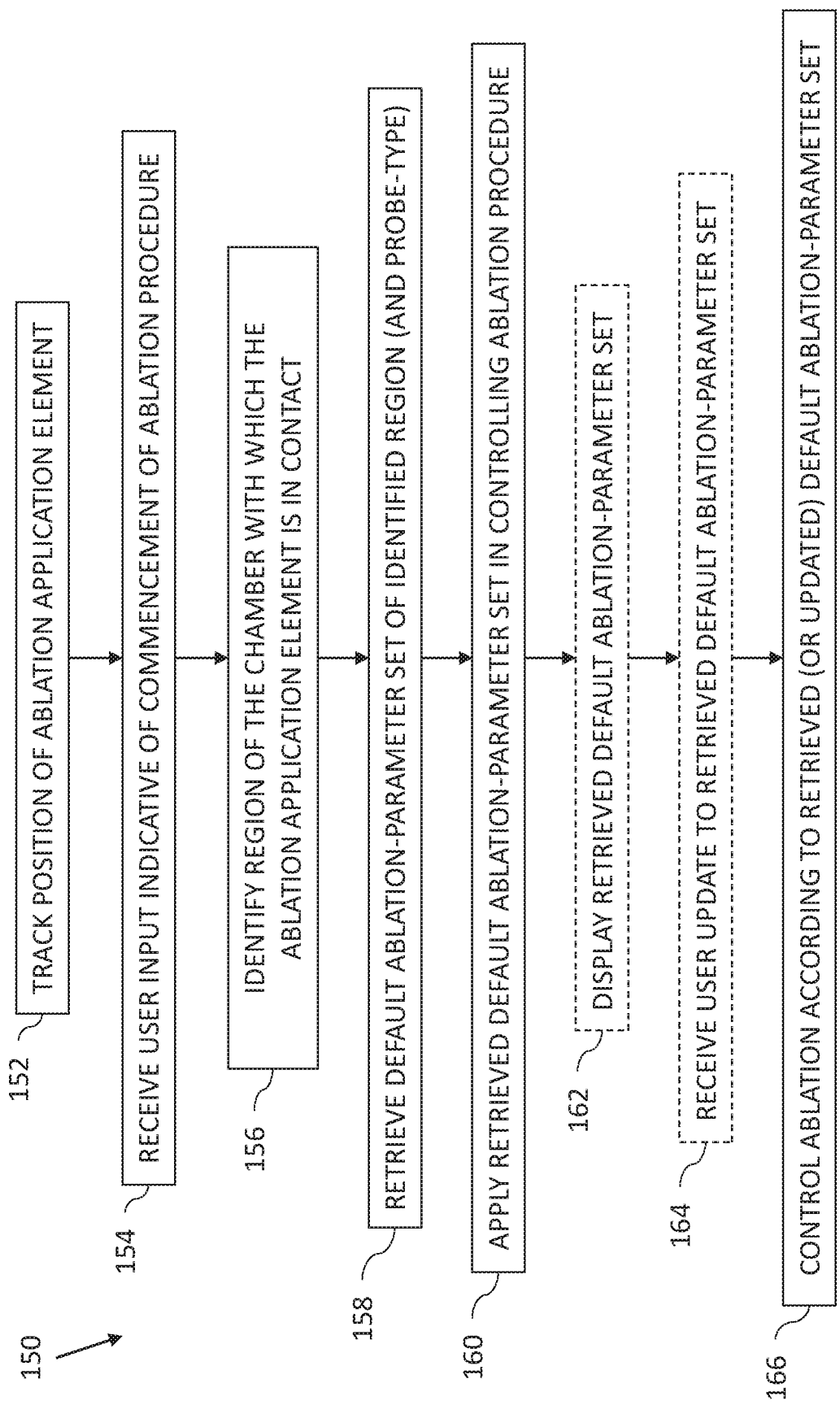
FIG. 8 is a flowchart including exemplary steps in an ablation method for use with the apparatus of FIG. 1.

Reference is now made to FIG. 8, which is a flowchart 150 including exemplary steps in an ablation method for use with the apparatus 12 of FIG. 1. After performing the preparatory method described above with reference to FIG. 3 and described in more detail with reference to FIGS. 4-7, the ablation procedure may commence. Preparation of the ablation probe 20 and inserting it into the chamber of the heart of the patient 18 was described in detail with reference to FIG. 1.

The tracking module 58 is configured to track (block 152) a position of the ablation application element(s) of the ablation probe 20 within the heart. The tracking module 58 was described in detail with reference to FIG. 1.

The processor 46 is configured to receive (block 154) a user input (via the input device 49 for example) indicative of commencement of an ablation procedure. The processor 46 is configured to identify (block 156), responsively to the tracked position, a region 88 of the chamber with which the ablation application element(s) is in contact. For example, the ablation application element(s) may be in contact with the septum of the left atrium. Responsively to the user input of the step of block 154, the processor 46 is configured to retrieve (block 158) the respective default ablation-parameter set assigned to the identified region. For example, the default ablation-parameter set for the septum of the left atrium is retrieved. In some embodiments, responsively to the user input of the step of block 154, the processor 46 is configured to retrieve the probe-specific default ablation-parameter set assigned to the identified region for the probe-type of the ablation probe. For example, the default ablation-parameter set of the septum of the left atrium for a balloon catheter is retrieved.

The processor 46 is configured to apply (block 160) the retrieved default ablation-parameter set in controlling the ablation procedure. The step of block 160 may include automatically accepting the retrieved default ablation-parameter set in controlling the ablation procedure or allowing a user (e.g., the physician 14) to inspect the retrieved settings and amend the settings prior to using the settings in the ablation procedure described in more detail with reference to the steps of blocks 162 and 164 below.

Therefore, in some embodiments, the processor 46 is configured to display (block 162), on the display 61, the retrieved default ablation-parameter set and receive (block 164), via the input device 49, a user update to the retrieved default ablation-parameter set yielding an updated ablation-parameter set. The processor 46 is configured to control ablation (block 166) by the ablation probe 20 of the tissue at the identified region according to the retrieved default ablation-parameter set (or according to the updated ablation-parameter set if the step of block 164 was performed).

Figure 9:
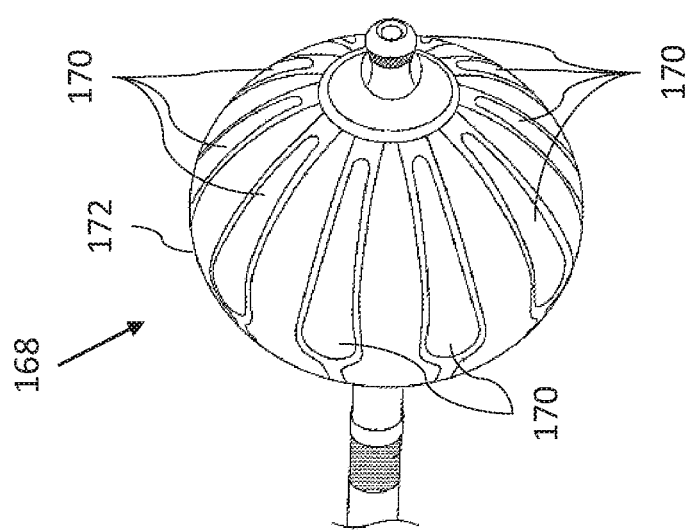
FIG. 9 is a schematic view of a balloon catheter for use with the apparatus of FIG. 1.

Reference is now made to FIG. 9, which is a schematic view of a balloon catheter 168 for use with the apparatus 12 of FIG. 1. The balloon catheter 168 is an ablation probe, which includes a multiplicity of ablation-application elements 170 (e.g., ablation electrodes) disposed around an equator of an inflatable balloon 172 of the balloon catheter 168. The balloon catheter 168 is particularly effective in simultaneously performing ablation at more than one site in the chamber of the heart.

Figure 10:
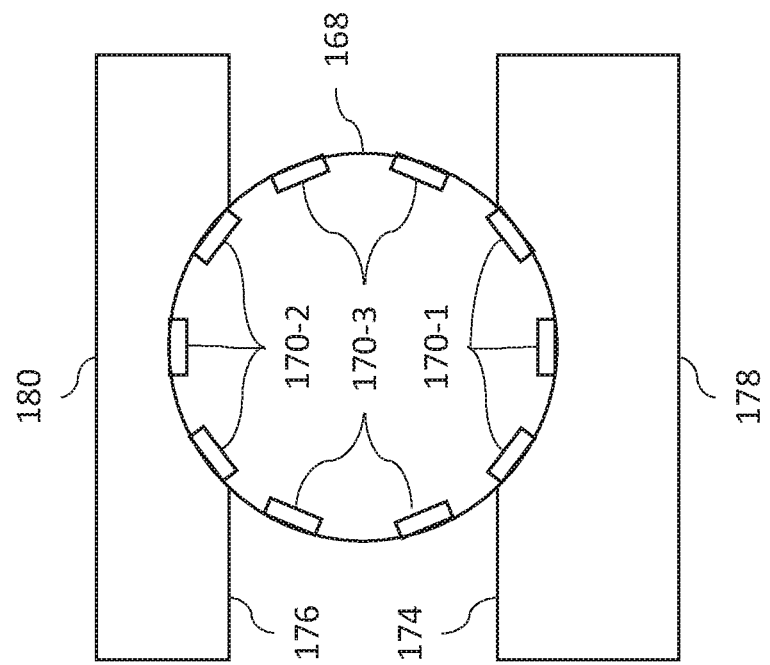
FIG. 10 is a cross-sectional view of the balloon catheter disposed in a chamber of a heart for use with the apparatus of FIG. 1.

Reference is now made to FIG. 10, which is a cross-sectional view of the balloon catheter 168 disposed in a chamber of a heart for use with the apparatus 12 of FIG. 1. Some of the ablation application elements 170-1 are in contract with a first tissue surface 174 of the chamber and some of the ablation application elements 170-2 are in contact with a second tissue surface 176 of the chamber, while some of the ablation application elements 170-3 are not in contact with any tissue. Additionally, a tissue 178 of the first tissue surface 174 is thicker than a tissue 180 of the second tissue surface 176. Therefore, when the balloon catheter 168 is actuated to perform ablation, the ablation application elements 170-1 should be set with a higher power and/or a longer ablation duration than the ablation application elements 170-2, while the ablation application elements 170-3 should not be activated at all. Applying the above settings may be very challenging for the physician 14.

In accordance with some embodiments of the present invention, different default ablation-parameter sets are retrieved for the ablation application elements 170-1 in contact with the first tissue surface 174 and for the ablation application elements 170-2 in contact with the second tissue surface 176 based on the tracked location of each of the ablation application elements 170. The ablation application elements 170-3 which are not currently in contact with any tissue are generally not actuated to prevent additional heat from being generated in the heart chamber. The above method is now described in more detail with reference to FIG. 11.

Figure 11:
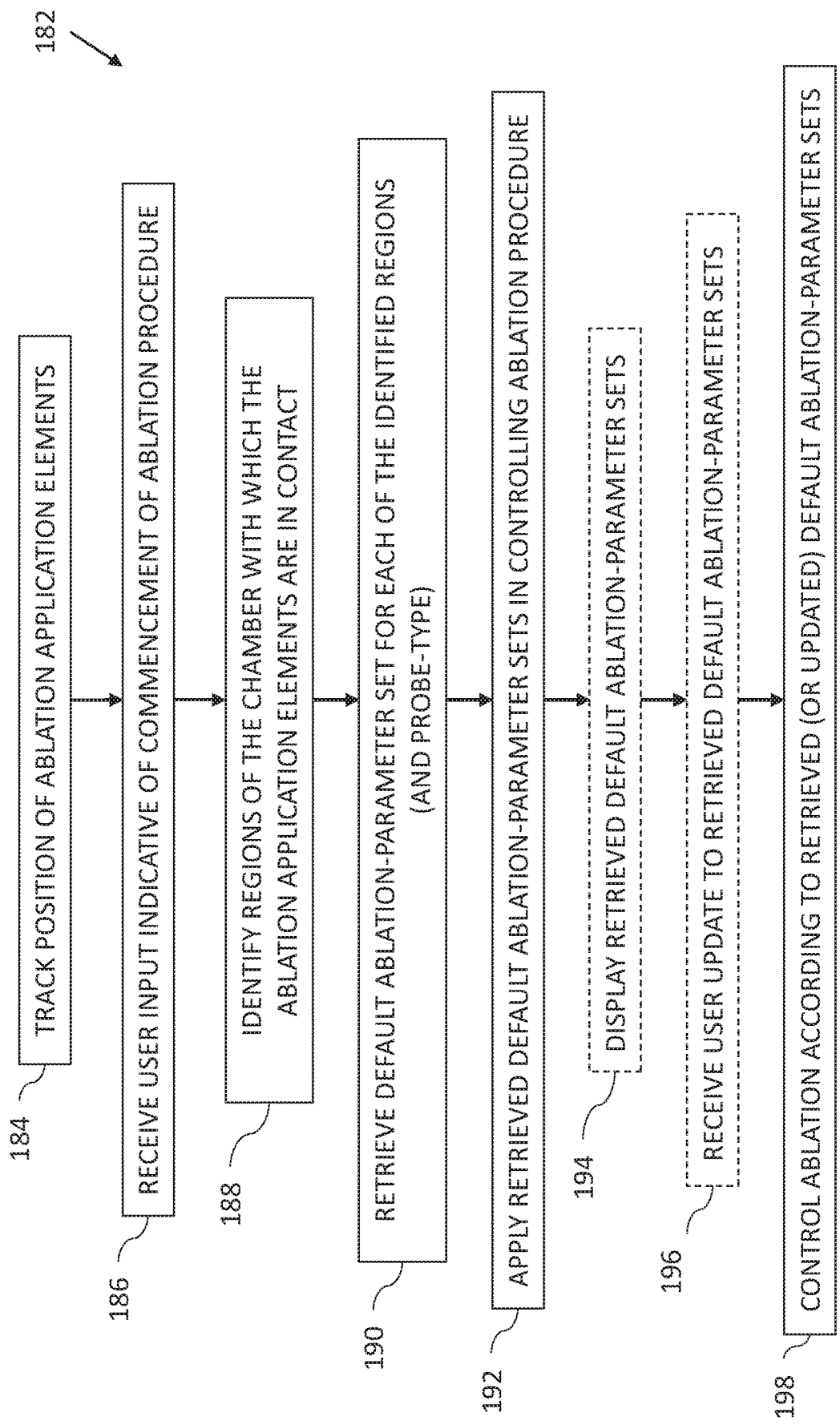
FIG. 11 is a flowchart including exemplary steps in an ablation method using a multi-ablation element probe for use with the apparatus of FIG. 1.

Reference is now made to FIG. 11, which is a flowchart 182 including exemplary steps in an ablation method using a multi-ablation-element probe (e.g., the balloon catheter 168 of FIG. 9 or any other suitable multi-ablation element probe) for use with the apparatus of FIG. 1.

The tracking module 58 is configured to track (block 184) a position of each of the ablation-application elements of the multi-ablation-element probe within the heart. The processor 46 is configured to receive (block 186) a user input (via the input device 49 for example) indicative of commencement of an ablation procedure.

The processor 46 is configured to identify (block 188), responsively to the tracked position of each of the ablation application elements, the regions 88 of the chamber with which the ablation application elements are in contact.

For example, the processor 46 is configured to identify, responsively to the tracked positions, a first region (e.g., the first tissue surface 174) of the chamber with which at least a first one of the multiplicity of ablation application elements (e.g., the ablation application elements 170-1 of FIG. 10) is/are in contact. The processor 46 is configured to identify, responsively to the tracked positions, a second region (e.g., the second tissue surface 176) of the chamber with which at least a second one of the multiplicity of ablation application elements (e.g., the ablation application elements 170-2 of FIG. 10) is/are in contact.

The processor 46 is configured to retrieve (block 190) the default ablation-parameter set assigned to each of the identified regions (e.g., the default ablation-parameter set assigned to the first region and the default ablation-parameter set assigned to the second region).

The processor 46 is configured to apply (block 192) the retrieved default ablation-parameter sets (e.g. the retrieved default ablation-parameter set of the first and second region) to perform the ablation procedure at the identified regions (e.g., the first and second region) using the corresponding ablation application elements (e.g., the first one and the second one of the multiplicity of ablation application elements, respectively).

The steps of blocks 194 and 196 broadly correspond to the steps of blocks 162 and 164, respectively, described above with reference to FIG. 8. The processor 46 is configured to control ablation (block 198) according to the retrieved (or updated) default ablation-parameter sets.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A cardiac ablation system, comprising:
    an ablation probe including at least one ablation application element configured to ablate tissue in a chamber of a heart of a living subject;
    a tracking module configured to track a position of the at least one ablation application element within the heart;
    a memory configured to store a map of the chamber of the heart and to store a different, respective default ablation-parameter set for each of a plurality of different regions of the chamber, each default ablation-parameter set corresponding to at least one of the plurality of regions and comprising a plurality of ablation-parameters; and
    processing circuitry configured to:
        segment, prior to ablation, the map of the chamber into the plurality of different regions, each region having an assigned regional designation;
        assign each of the default ablation-parameter sets to each of the plurality of different regions respectively based upon the regional designation of the identified region;
        receive a user input indicative of commencement of an ablation procedure;
        identify, responsively to the tracked position, one of the plurality of regions with which the at least one ablation application element is in contact;
        responsively to the user input, retrieve the respective stored default ablation-parameter set assigned to the identified region based upon the regional designation of the identified region; and
        apply the retrieved stored default ablation-parameter set corresponding to the regional designation of the identified region in controlling the ablation procedure in the identified region.

2. The system according to claim 1, wherein the processing circuitry is configured to apply a segmented model of a heart chamber to the map of the chamber yielding a segmented map of the chamber.

3. The system according to claim 2, wherein the processing circuitry is configured to:
    receive at least one user correction to a segmentation of the segmented map; and responsively to the received at least one user correction, amend the segmented map.

4. The system according to claim 1, wherein the processing circuitry is configured to:
    receive a user markup of the map of the chamber dividing the map into the different regions; and
    responsively to the received user markup, segment the map of the chamber into the different regions.

5. The system according to claim 1, wherein the processing circuitry is configured to:
    receive user-defined default ablation-parameter sets for each of the different regions; and responsively to a regional designation of each of the received user-defined default ablation-parameter sets, assign the user-defined default ablation-parameter sets to the different regions.

6. The system according to claim 1, wherein the processing circuitry is configured to control ablation by the ablation probe of the tissue at the identified region according to the retrieved default ablation-parameter set.

7. The system according to claim 1, wherein the processing circuitry is configured to:
receive a user update to the retrieved default ablation-parameter set yielding an updated ablation-parameter set; and
control ablation by the ablation probe of the tissue at the identified region according to the updated ablation-parameter set.

8. The system according to claim 1, wherein the processing circuitry is configured to:
assign a probe-specific default ablation-parameter set to each of the different regions for a plurality of different probe-types; and
responsively to the user input, retrieve the probe-specific default ablation-parameter set assigned to the identified region for a probe-type of the ablation probe.

9. The system according to claim 1, wherein:
the ablation probe includes a multiplicity of ablation application elements; and
the processing circuitry is configured to:
identify, responsively to the tracked position, a first region of the chamber with which at least a first one of the multiplicity of ablation application elements is in contact;
identify, responsively to the tracked position, a second region of the chamber with which at least a second one of the multiplicity of ablation application elements is in contact;
retrieve the default ablation-parameter set assigned to the first region and the default ablation-parameter set assigned to the second region; and
apply the retrieved default ablation-parameter set of the first and second region to perform the ablation procedure at the first and second region using the first one and the second one of the multiplicity of ablation application elements, respectively.

10. The system according to claim 1, wherein the default ablation-parameter set for one region of the different regions includes any one or more of the following: a tissue thickness of the one region; whether to track temperature during the ablation procedure; an ablation mode to use during the ablation procedure; an irrigation rate to use during the ablation procedure; a power level to apply during the ablation procedure; a force to apply during the ablation procedure; an ablation duration of the ablation procedure; an ablation index to use during the ablation procedure; a target power; and a target temperature.

11. The system according to claim 10, wherein the ablation mode is selected from any one or more of the following: ablation index mode; controlling ablation power according to a measured temperature; applying an alternating current to the at least one ablation application element; applying a direct current to the at least one ablation application element; laser ablation; electroporation; cryoablation; radio-frequency power ablation.

12. A cardiac ablation method, comprising:
tracking a position of at least one ablation application element of an ablation probe configured to ablate tissue in a chamber of a heart of a living subject;
storing a map of the chamber of the heart;
storing a different, respective default ablation-parameter set for each of a plurality of different regions of the chamber, each default ablation-parameter set corresponding to at least one of the plurality of regions and comprising a plurality of ablation-parameters;
segmenting, prior to ablation, the map of the chamber into the plurality of different regions, each region having a regional designation;
assigning each of the default ablation-parameter sets to each of the plurality of different regions respectively based upon the regional designation of the identified region;
receiving a user input indicative of commencement of an ablation procedure;
identifying, responsively to the tracked position, one of the plurality of regions with which the at least one ablation application element is in contact;
responsively to the user input, retrieve the respective stored default ablation-parameter set assigned to the identified region based upon the regional designation of the identified region; and
applying the retrieved stored default ablation-parameter set corresponding to the regional designation of the identified region in controlling the ablation procedure in the identified region.

13. The method according to claim 12, further comprising applying a segmented model of a heart chamber to the map of the chamber yielding a segmented map of the chamber.

14. The method according to claim 13, further comprising:
receiving at least one user correction to a segmentation of the segmented map; and
responsively to the receiving the at least one user correction, amending the segmented map.

15. The method according to claim 12, further comprising:
receiving a user markup of the map of the chamber dividing the map into the different regions; and
responsively to the receiving the user markup, segmenting the map of the chamber into the different regions.

16. The method according to claim 12, further comprising:
receiving user-defined default ablation-parameter sets for each of the different regions; and
responsively to a regional designation of each of the received user-defined default ablation-parameter sets, assigning the user-defined default ablation-parameter sets to the different regions.

17. The method according to claim 12, further comprising controlling ablation by the ablation probe of the tissue at the identified region according to the retrieved default ablation-parameter set.

18. The method according to claim 12, further comprising:
receiving a user update to the retrieved default ablation-parameter set yielding an updated ablation-parameter set; and
controlling ablation by the ablation probe of the tissue at the identified region according to the updated ablation-parameter set.

19. The method according to claim 12, further comprising:
assigning a probe-specific default ablation-parameter set to each of the different regions for a plurality of different probe-types; and responsively to the user input, retrieving the probe-specific default ablation-parameter set assigned to the identified region for a probe-type of the ablation probe.

20. The method according to claim 12, wherein:
the ablation probe includes a multiplicity of ablation application elements; and the method further comprises:
identifying, responsively to the tracked position, a first region of the chamber with which at least a first one of the multiplicity of ablation application elements is in contact;
identifying, responsively to the tracked position, a second region of the chamber with which at least a second one of the multiplicity of ablation application elements is in contact;
retrieving the default ablation-parameter set assigned to the first region and the default ablation-parameter set assigned to the second region; and
applying the retrieved default ablation-parameter set of the first and second region to perform the ablation procedure at the first and second region using the first one and the second one of the multiplicity of ablation application elements, respectively.

21. The method according to claim 12, wherein the default ablation-parameter set for one region of the different regions includes any one or more of the following: a tissue thickness of the one region; whether to track temperature during the ablation procedure; an ablation mode to use during the ablation procedure; an irrigation rate to use during the ablation procedure; a power level to apply during the ablation procedure; a force to apply during the ablation procedure; an ablation duration of the ablation procedure; an ablation index to use during the ablation procedure; a target power; and a target temperature.

22. The method according to claim 21, wherein the ablation mode is selected from any one or more of the following: ablation index mode; controlling ablation power according to a measured temperature; applying an alternating current to the at least one ablation application element; applying a direct current to the at least one ablation application element; laser ablation; electroporation; cryoablation; radio-frequency power ablation.

23. A software product, comprising a non-transient computer-readable medium in which program instructions are stored, which instructions, when read by a central processing unit (CPU), cause the CPU to:
track a position of at least one ablation application element of an ablation probe configured to ablate tissue in a chamber of a heart of a living subject;
store a map of the chamber of the heart;
store a different, respective default ablation-parameter set for each of a plurality of different regions of the chamber, each default ablation-parameter set corresponding to at least one of the plurality of regions and comprising a plurality of ablation-parameters;
segment, prior to ablation, the map of the chamber into the plurality of different regions, each region having a regional designation;
assign each of the default ablation-parameter sets to each of the plurality of different regions respectively based upon the regional designation of the identified region;
receive a user input indicative of commencement of an ablation procedure;
identify, responsively to the tracked position, one of the plurality of regions with which the at least one ablation application element is in contact;
responsively to the user input, retrieve the respective stored default ablation-parameter set assigned to the identified region based upon the regional designation of the identified region; and
apply the retrieved stored default ablation-parameter set corresponding to the regional designation of the identified region in controlling the ablation procedure in the identified region.

* * * * *